(12) United States Patent
Nogueira et al.

(10) Patent No.: US 9,227,063 B2
(45) Date of Patent: Jan. 5, 2016

(54) METHODS AND SYSTEMS FOR LOWERING A PITCH SENSATION AS PERCEIVED BY A COCHLEAR IMPLANT PATIENT

(71) Applicant: ADVANCED BIONICS AG, Staefa (CH)

(72) Inventors: Waldo Nogueira, Hannover (DE); Leonid M. Litvak, Los Angeles, CA (US); Aniket Saoji, Ann Arbor, MI (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/361,251

(22) PCT Filed: Nov. 28, 2012

(86) PCT No.: PCT/US2012/066892
§ 371 (c)(1),
(2) Date: May 28, 2014

(87) PCT Pub. No.: WO2013/082185
PCT Pub. Date: Jun. 6, 2013

(65) Prior Publication Data
US 2014/0336725 A1 Nov. 13, 2014

Related U.S. Application Data

(60) Provisional application No. 61/565,361, filed on Nov. 30, 2011.

(51) Int. Cl.
*A61N 1/36* (2006.01)
*A61N 1/05* (2006.01)
(Continued)

(52) U.S. Cl.
CPC .......... *A61N 1/36032* (2013.01); *A61N 1/0541* (2013.01); *A61N 1/37252* (2013.01); *H04R 25/50* (2013.01)

(58) Field of Classification Search
CPC .................... A61N 1/36032; A61N 1/0541
See application file for complete search history.

(56) References Cited

U.S. PATENT DOCUMENTS

| | | |
|---|---|---|
| 6,219,580 B1 | 4/2001 | Faltys et al. |
| 6,778,858 B1 | 8/2004 | Peeters |

(Continued)

FOREIGN PATENT DOCUMENTS

| | | |
|---|---|---|
| WO | WO-2008/154706 | 12/2008 |
| WO | WO-2010/009010 | 1/2010 |

(Continued)

OTHER PUBLICATIONS

Olivier Macherey, et al., "Asymmetric Pulses in Cochlear Implants: Effects of Pulse Shape, Polarity, and Rate", *Journal of the Association for Research in Otolaryngology 7:253-266*, (2006).

(Continued)

*Primary Examiner* — Theodore Stigell
*Assistant Examiner* — Natasha Patel
(74) *Attorney, Agent, or Firm* — ALG Intellectual Property, LLC

(57) ABSTRACT

An exemplary method of lowering a pitch sensation as perceived by a cochlear implant patient includes 1) identifying a most apical electrode included in a plurality of electrodes disposed within a cochlea of the patient, 2) directing a cochlear implant communicatively coupled to the plurality of electrodes to apply one or more anodecathode biphasic stimulation pulses to the most apical electrode during a stimulation period, and 3) directing the cochlear implant to apply one or more cathode-anode biphasic stimulation pulses to one or more other electrodes included in the plurality of electrodes during the stimulation period. Corresponding methods and systems are also disclosed.

20 Claims, 11 Drawing Sheets

(51) Int. Cl.
*A61N 1/372* (2006.01)
*H04R 25/00* (2006.01)

(56) References Cited

U.S. PATENT DOCUMENTS

| | | |
|---|---|---|
| 7,167,754 B1 | 1/2007 | Peeters et al. |
| 7,889,879 B2 | 2/2011 | Dillon et al. |
| 2009/0264960 A1 | 10/2009 | Litvak et al. |
| 2010/0161000 A1 | 6/2010 | Litvak et al. |
| 2012/0130449 A1* | 5/2012 | Carlyon et al. ......... 607/57 |

FOREIGN PATENT DOCUMENTS

| | | |
|---|---|---|
| WO | WO-2010/150002 | 12/2010 |
| WO | WO-2011/140454 | 11/2011 |

OTHER PUBLICATIONS

International Search Report and Written Opinion received in International Application No. PCT/US12/066892, dated Aug. 28, 2013.

* cited by examiner

METHODS AND SYSTEMS FOR LOWERING A PITCH SENSATION AS PERCEIVED BY A COCHLEAR IMPLANT PATIENT

RELATED APPLICATIONS

The present application claims priority to U.S. Provisional Patent Application No. 61/565,361 by Waldo Nogueira et al., filed on Nov. 30, 2011, and entitled "Methods and Systems for Lowering a Pitch Sensation as Perceived by a Cochlear Implant Patient," the contents of which are hereby incorporated by reference in their entirety.

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

Unfortunately, conventional cochlear implant systems cannot present a full spectrum of audible sound to the patient. For example, there are often sounds that have pitches lower than those which can be conventionally generated by applying electrical stimulation to one or more electrodes disposed within the cochlea of a patient. This is especially the case when ossification, malformations within the cochlea, and/or other anatomical anomalies prevent full insertion and/or function of an electrode lead within the cochlea.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
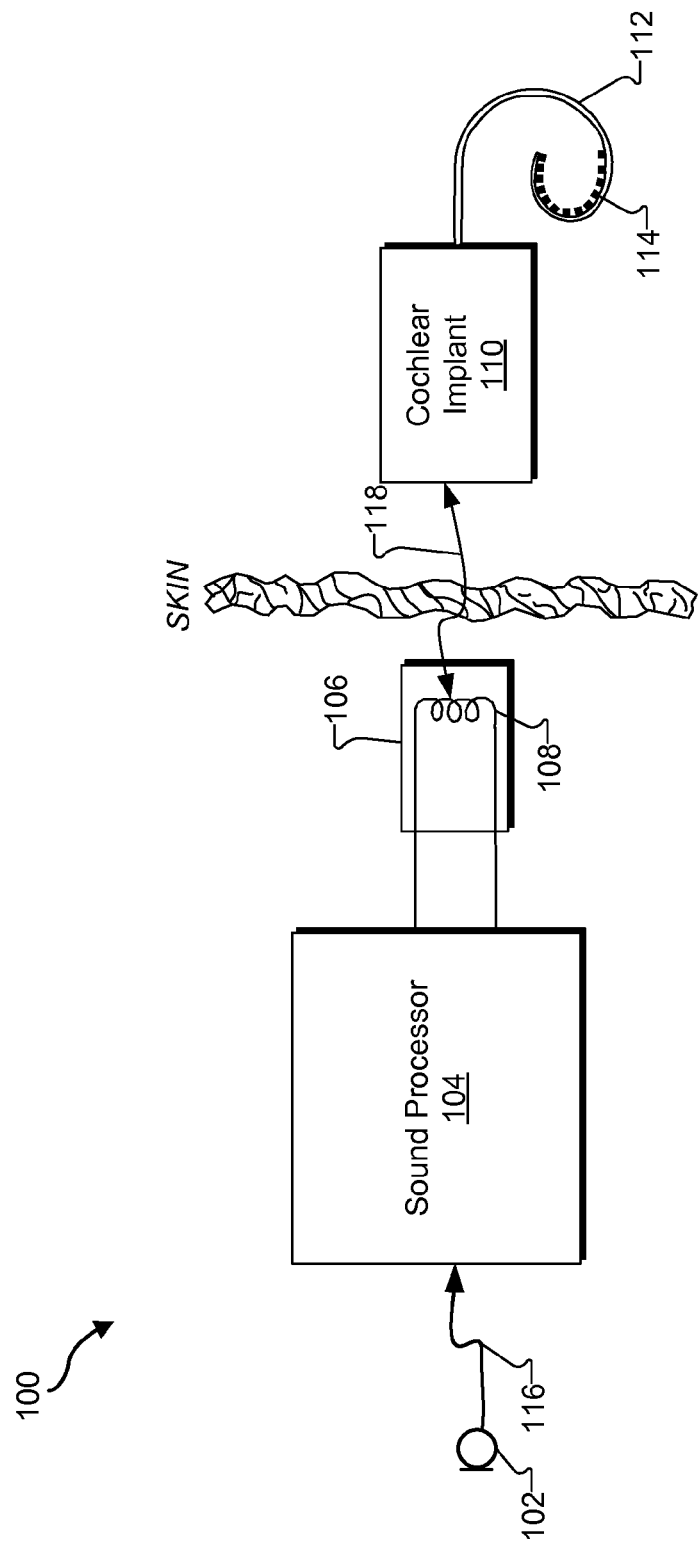
FIG. 1 illustrates an exemplary cochlear implant system according to principles described herein.

Methods and systems for lowering a pitch sensation as perceived by a cochlear implant patient are described herein. As will be described below, a sound processor may identify a most apical electrode (i.e., the electrode most closely located to the apex of the cochlea) included in a plurality of electrodes disposed within a cochlea of a patient, direct a cochlear implant communicatively coupled to the plurality of electrodes to apply one or more anode-cathode biphasic stimulation pulses to the most apical electrode (and, in some examples, one or more electrodes adjacent to the most apical electrode) during a stimulation period, and direct the cochlear implant to apply one or more cathode-anode biphasic stimulation pulses to one or more other electrodes included in the plurality of electrodes during the same stimulation period.

As used herein, an "anode-cathode biphasic stimulation pulse" refers to an electrical stimulation pulse that may be applied to an electrode (e.g., in a monopolar configuration) and that includes a first phase that is positive followed by a second phase that is negative. Conversely, a "cathode-anode biphasic stimulation pulse" refers to an electrical stimulation pulse that may be applied to an electrode (e.g., in a monopolar configuration) and that includes a first phase that is negative followed by a second phase that is positive. Exemplary anode-cathode biphasic stimulation pulses and cathode-anode biphasic stimulation pulses will be described in more detail below.

It has been found that by applying anode-cathode biphasic stimulation pulses to the most apical electrode, the range of pitches or frequencies that may be presented to a cochlear implant patient may be expanded. For example, the anode-cathode biphasic stimulation pulses may result in the cochlear implant patient perceiving a pitch lower than that associated with the most apical electrode in conventional stimulation strategies (i.e., strategies that apply cathode-anode biphasic stimulation pulses to each electrode disposed within the cochlea of a patient).

Lowering a pitch sensation as perceived by a cochlear implant patient in this manner may be beneficial in a variety of different situations. For example, the patient may desire to listen to music and/or other audio content that spans a relatively large spectrum. The methods and systems described herein may be used to allow the patient to perceive lower pitches than that which he or she would normally be able to perceive, thereby enhancing the quality of his or her listening experience. Additionally or alternatively, the methods and systems described herein may be beneficial when ossification, malformations within the cochlea, and/or other anatomical anomalies prevent full insertion and/or function of an electrode lead within the cochlea of a patient. This is because a partially inserted electrode lead may not be fully in communication with an apical region of the cochlea (which region is associated with relatively low pitches).

FIG. 1 illustrates an exemplary cochlear implant system 100. Cochlear implant system 100 may include a microphone 102, a sound processor 104, a headpiece 106 having a coil 108 disposed therein, a cochlear implant 110, and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct cochlear implant 110 to generate and apply electrical stimulation (also referred to herein as "stimulation current") to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the audio signal detected by microphone 102 in accordance with a selected sound processing strategy or program to generate appropriate stimulation parameters for controlling cochlear implant 110. Sound processor 104 may include or be implemented by a behind-the-ear ("BTE") unit, a body worn device, a portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to cochlear implant 110 with coil 108 by way of a communication link 118. These control parameters may be configured to specify one or more stimulation parameters, operating parameters, and/or any other parameter by which cochlear implant 110 is to operate as may serve a particular implementation. Exemplary control parameters include, but are not limited to, stimulation current levels, volume control parameters, program selection parameters, operational state parameters (e.g., parameters that turn a sound processor and/or a cochlear implant on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar stimulation parameters), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within cochlear implant 110. In this manner, control parameters and power signals may be wirelessly transmitted between sound processor 104 and cochlear implant 110 via communication link 118. It will be understood that data communication link 118 may include a bi-directional communication link and/or one or more dedicated uni-directional communication links. In some alternative embodiments, sound processor 104 and cochlear implant 110 may be directly connected with one or more wires or the like.

Cochlear implant 110 may include any suitable cochlear implant as may serve a particular implementation. For example, cochlear implant 110 may include an implantable cochlear stimulator, a brainstem implant and/or any other type of cochlear implant that may be implanted within a patient and configured to apply electrical stimulation to one or more stimulation sites located along an auditory pathway of the patient.

In some examples, cochlear implant 110 may be configured to generate electrical stimulation representative of an audio signal detected by microphone 102 in accordance with one or more stimulation parameters transmitted thereto by sound processor 104. Cochlear implant 110 may be further configured to apply the electrical stimulation to one or more stimulation sites within the patient via one or more electrodes 114 disposed along lead 112. In some examples, cochlear implant 110 may include a plurality of independent current sources each associated with a channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by cochlear implant 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the one or more stimulation sites. Any number of electrodes 114 (e.g., sixteen) may be disposed on lead 112 as may serve a particular implementation.

Figure 2:
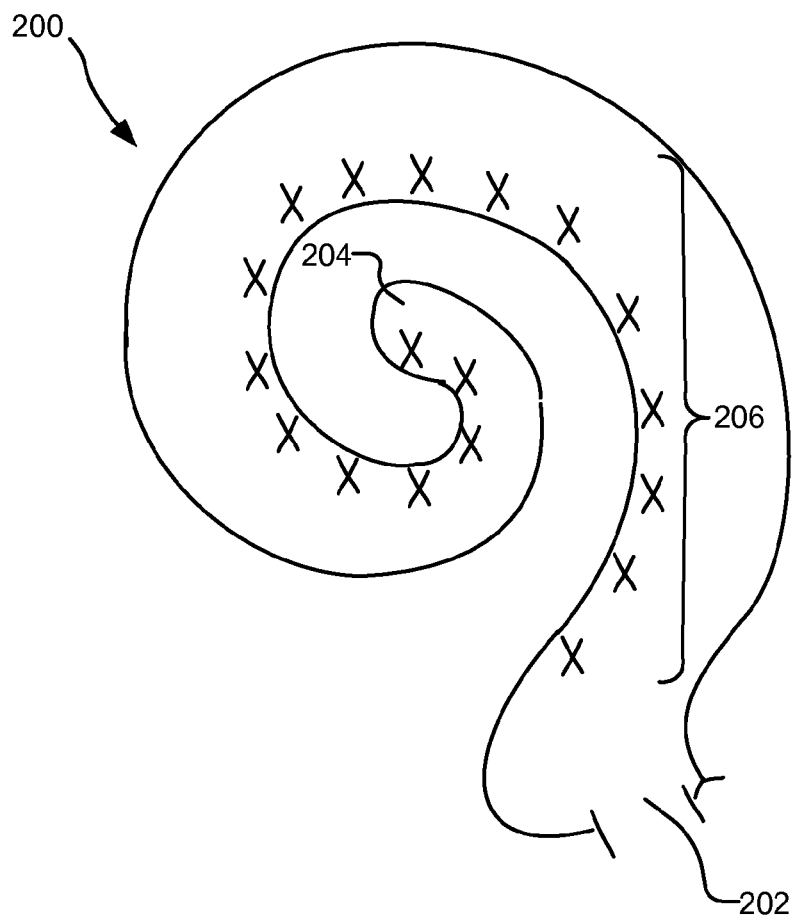
FIG. 2 illustrates a schematic structure of the human cochlea.

FIG. 2 illustrates a schematic structure of the human cochlea 200 into which lead 112 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
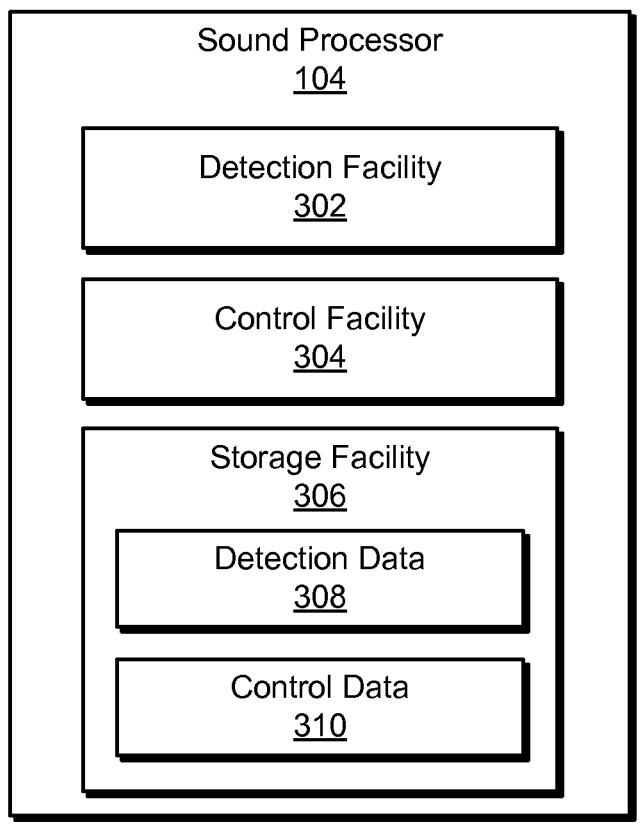
FIG. 3 illustrates exemplary components of a sound processor according to principles described herein.

FIG. 3 illustrates exemplary components of sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include a detection facility 302, a control facility 304, and a storage facility 306, which may be in communication with one another using any suitable communication technologies. One or more of facilities 302-306 may include a computing device or processor configured to perform one or more of the functions described herein. Facilities 302-306 will now be described in more detail.

Detection facility 302 may be configured to identify a most apical electrode included in a plurality of electrodes disposed within a cochlea of a patient. This may be performed in any suitable manner. For example, detection facility 302 may designate a functioning electrode that is closest to the apex of the cochlea as being the most apical electrode.

Figure 4:
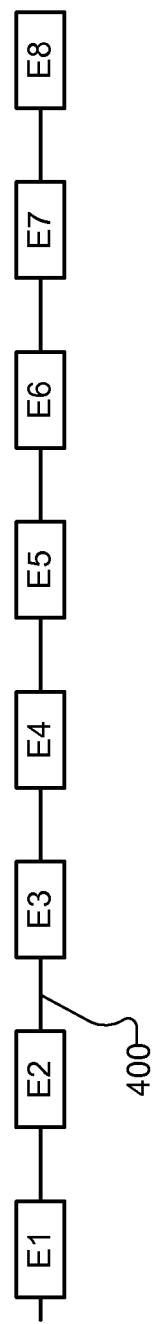
FIG. 4 shows an exemplary lead that may include a plurality of electrodes disposed thereon according to principles described herein.

To illustrate, FIG. 4 shows an exemplary lead 400 that may include a plurality of electrodes (e.g., electrodes E1 through E8) disposed thereon. While eight electrodes are shown to be disposed on lead 400 in FIG. 4, it will be recognized that lead 400 may alternatively include any other number of electrodes disposed thereon as may serve a particular implementation.

In some examples, lead 400 may be inserted within the cochlea of a patient and communicatively coupled to cochlear implant 110 such that cochlear implant 110 may deliver one or more electrical stimulation pulses to one or more of electrodes E1-E8. For example, lead 400 may be inserted within the cochlea until one or more electrodes disposed on a distal portion of lead 400 (e.g., electrodes E6-E8) are in communication with the apical region of the cochlea. In this example, because electrode E8 is the most distally located electrode on lead 400, detection facility 302 may perform one or more tests to verify that it is a functioning electrode. If detection facility 302 verifies that electrode E8 is a functioning electrode, detection facility 302 may designate it as being the most apical electrode. However, if electrode E8 is not a functioning electrode (e.g., if electrode E8 is malfunctioning and/or or disabled for any reason), detection facility 302 may identify another functioning electrode (electrode E7) as being the most apical electrode.

Returning to FIG. 3, control facility 304 may be configured to perform one or more operations associated with a control of cochlear implant 110. For example, control facility 304 may direct cochlear implant 110 to apply one or more anode-cathode biphasic stimulation pulses to the most apical electrode during a stimulation period. Control facility 304 may be further configured to direct cochlear implant 110 to direct the cochlear implant to apply one or more cathode-anode biphasic stimulation pulses to one or more other electrodes included in the plurality of electrodes that are disposed within the cochlea during the stimulation period. As used herein, a "stimulation period" refers to any period of time during which electrical stimulation is applied to one or more stimulation sites within a cochlear implant patient. For example, a stimulation period may correspond to a period of time during which a particular type of audio content (e.g., a song) is applied to the patient.

Figure 5:
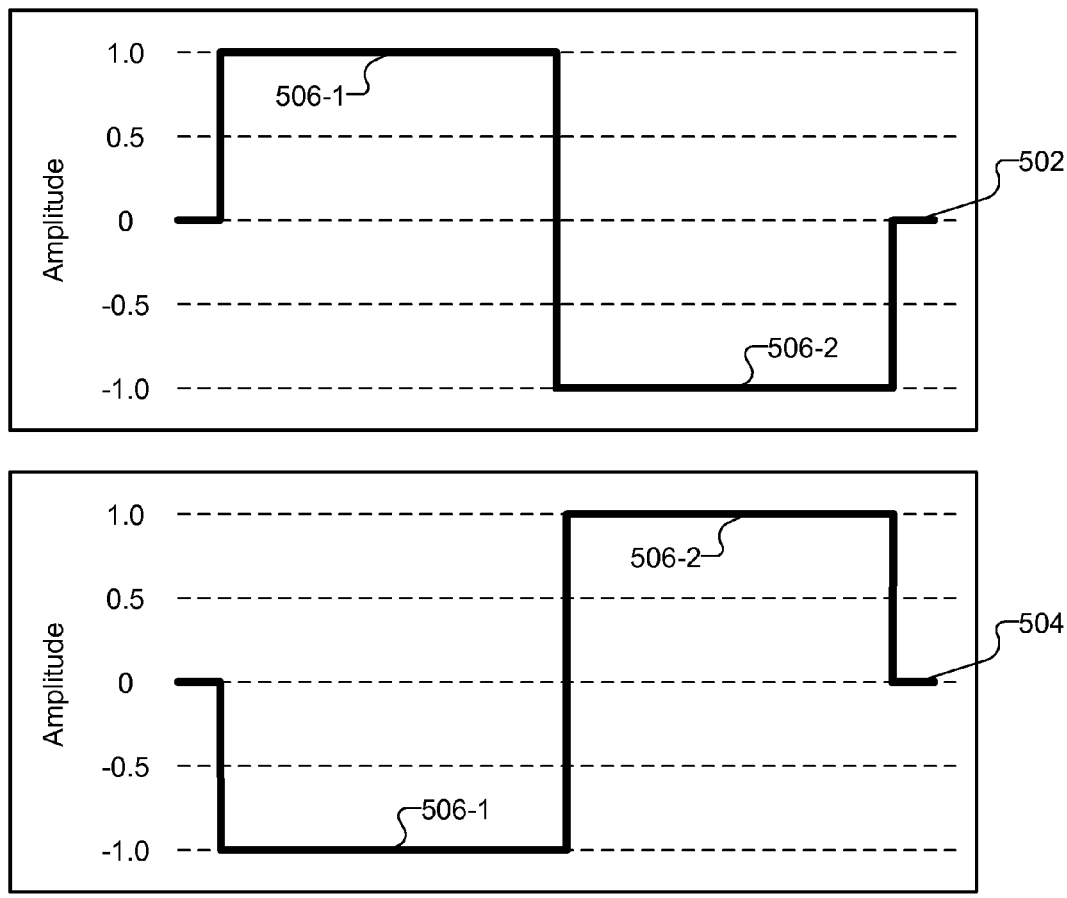
FIG. 5 illustrates an exemplary anode-cathode biphasic stimulation pulse and an exemplary cathode-anode biphasic stimulation pulse according to principles described herein.

FIG. 5 illustrates an exemplary anode-cathode biphasic stimulation pulse 502 that may be applied to the most apical electrode included in a plurality of electrodes disposed within the cochlea of a patient during a stimulation period and an exemplary cathode-anode biphasic stimulation pulse 504 that may be applied to one or more other electrodes included in the plurality of electrodes during the stimulation period. As shown, anode-cathode biphasic stimulation pulse 502 includes a positive phase 506-1 (i.e., a phase having an amplitude that is positive) followed by a negative phase 506-2 (i.e., a phase having an amplitude that is negative). Conversely, cathode-anode biphasic stimulation pulse 504 includes a negative phase 508-1 followed by a positive phase 508-2.

In some examples, as illustrated in FIG. 5, the one or more anode-cathode biphasic stimulation pulses that are applied to the most apical electrode and the one or more cathode-anode biphasic stimulation pulses that are applied to the one or more other electrodes may have substantially equivalent amplitudes and pulse widths. However, in some alternative embodiments, the amplitudes and/or pulse widths may differ by any suitable amount as may serve a particular implementation.

As mentioned, application of anode-cathode biphasic stimulation pulses to the most apical electrode during a stimulation period (and, in some examples and as will be described in more detail below, one or more other electrodes disposed in the apical region of the cochlea) may result in the cochlear implant patient perceiving a pitch lower (or otherwise different) than that associated with the most apical electrode in conventional stimulation strategies (i.e., strategies that apply cathode-anode biphasic stimulation pulses to each electrode disposed within the cochlea of a patient). By applying cathode-anode biphasic stimulation pulses to one or more other electrodes within the cochlea of a patient (e.g., all of the electrodes that are not the most apical electrode) during the same stimulation period, various benefits associated with cathode-anode biphasic stimulation may be maintained. For example, cathode-anode biphasic stimulation may be relatively more effective in the basal region of the cochlea for some cochlear implant patients than anode-cathode biphasic stimulation. To illustrate, cathode-anode biphasic stimulation in the basal region may facilitate more effective representation of relatively high pitches than anode-cathode biphasic stimulation. Moreover, many cochlear implant patients are already accustomed to cathode-anode biphasic stimulation. Hence, preservation of cathode-anode biphasic stimulation in the basal region may allow a cochlear implant patient to more effectively and efficiently adjust to anode-cathode biphasic stimulation in the apical region.

Figure 6:
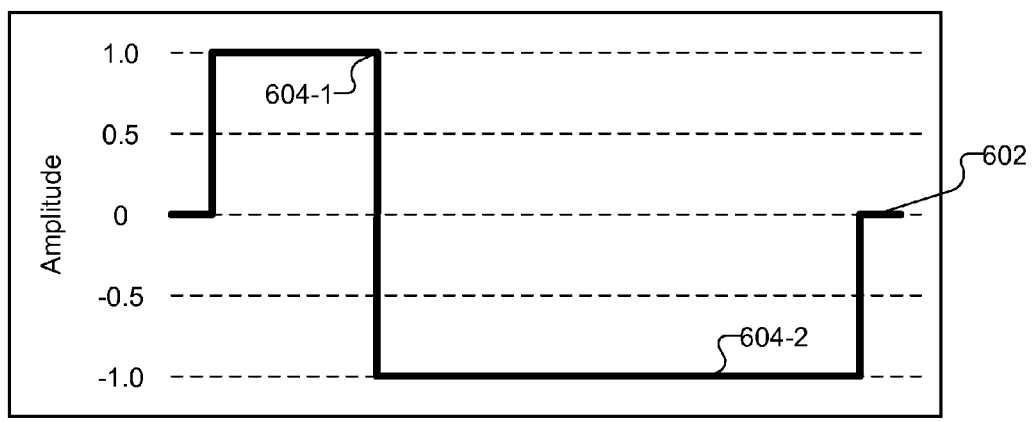
FIG. 6 shows an exemplary anode-cathode biphasic stimulation pulse that has a negative phase that is longer in duration than a positive phase of the anode-cathode biphasic stimulation pulse according to principles described herein.

In some examples, an anode-cathode biphasic stimulation pulse applied to the most apical electrode may be symmetric (i.e., the positive and negative phases have substantially equivalent durations as shown in FIG. 5). However, in some alternative embodiments, the durations of the positive and negative phases of an anode-cathode biphasic stimulation pulse applied to the most apical electrode may differ. For example, FIG. 6 shows an exemplary anode-cathode biphasic stimulation pulse 602 that may be used in accordance with the methods and systems described herein and that has a negative phase 604-2 that is longer in duration than a positive phase 604-1 of the anode-cathode biphasic stimulation pulse 602. In some examples, the duration of the negative phase 604-2 is at least twice as long as the duration of the positive phase 604-1.

By directing cochlear implant 110 to apply one or more asymmetric anode-cathode biphasic stimulation pulses, such as pulse 602, to the most apical electrode, control facility 304 may lower the pitch sensation perceived by some patients even more than that which can be achieved with one or more symmetric anode-cathode biphasic stimulation pulses. It will be recognized, however, that the change in pitch sensation that may result by using asymmetric anode-cathode biphasic stimulation may vary from patient to patient and that the duration of the positive and negative phases may be adjusted by a clinician and/or control facility 304 in order to optimize an operation of cochlear implant 110.

Returning to FIG. 3, control facility 304 may be further configured to direct cochlear implant 110 to dynamically switch between applying anode-cathode biphasic stimulation pulses to the most apical electrode and applying cathode-anode biphasic stimulation pulses to the most apical electrode. The dynamic switching may be performed in response to a change in an auditory scene associated with the patient and/or in response to any other factor as may serve a particular implementation.

As used herein, an "auditory scene" refers to a particular auditory or listening environment of a cochlear implant patient. For example, an auditory scene may be representative of a scene in which the patient is listening primarily to music, a scene in which the patient is primarily listening to speech, a crowded restaurant, wind, noise from an airplane or automobile, a quiet bedroom, and/or any other auditory environment that a cochlear implant patient may experience.

For example, detection facility 302 may detect a particular auditory scene in which an expanded range of pitches that may be presented to a patient is desirable (e.g., an auditory scene in which the patient is listening primarily to music). In response, control facility 304 may direct cochlear implant 110 to switch to applying anode-cathode biphasic stimulation pulses to the most apical electrode. Subsequently, detection facility 302 may detect that a change in the auditory scene to an auditory scene in which an expanded range of pitches is relatively not so important (e.g., a change to an auditory scene in which the patient is listening primarily to speech). In response, control facility 304 may direct cochlear implant 110 to switch back to applying cathode-anode biphasic stimulation pulses to the most apical electrode.

Detection facility 302 may detect an auditory scene (and/or a change in an auditory scene) in accordance with a predefined detection heuristic. An example of such a heuristic is a heuristic based on a band-by-band spectral power time variance of the power spectrum. Additionally or alternatively, an auditory scene may be detected in response to patient input. For example, a patient may recognize a particular auditory scene and provide detection facility 302 with one or more user commands representative of the auditory scene.

As mentioned, anode-cathode biphasic stimulation pulses may additionally be applied to one or more other electrodes disposed in the apical region of the cochlea. To this end, detection facility 302 may identify a group of one or more additional electrodes (e.g., a group of one or more electrodes adjacent to the most apical electrode) and designate these electrodes as apical electrodes (i.e., as being disposed within the apical region of the cochlea). In response, control facility 304 may direct cochlear implant 110 to apply one or more anode-cathode biphasic stimulation pulses to designated apical electrodes.

In some examples, anode-cathode biphasic stimulation may be used in conjunction with one or more other stimulation strategies or heuristics configured to expand a range of pitches that may be presented to a cochlear implant patient. For example, control facility 304 may be configured to direct cochlear implant 110 to apply one or more anode-cathode biphasic stimulation pulses to the most apical electrode in conjunction with a phantom electrode stimulation sound processing program.

As used herein, "phantom electrode stimulation" refers to another stimulation strategy that may be used to expand a range of pitches or frequencies that may be presented to a cochlear implant patient. In phantom electrode stimulation, compensation current is applied to one or more compensating electrodes in order to produce sound having a pitch that is lower than a pitch associated with a particular electrode (e.g., the most apical electrode) or a sound having a pitch that is higher than a pitch associated with a particular electrode (e.g., the most basal electrode).

Figure 7:
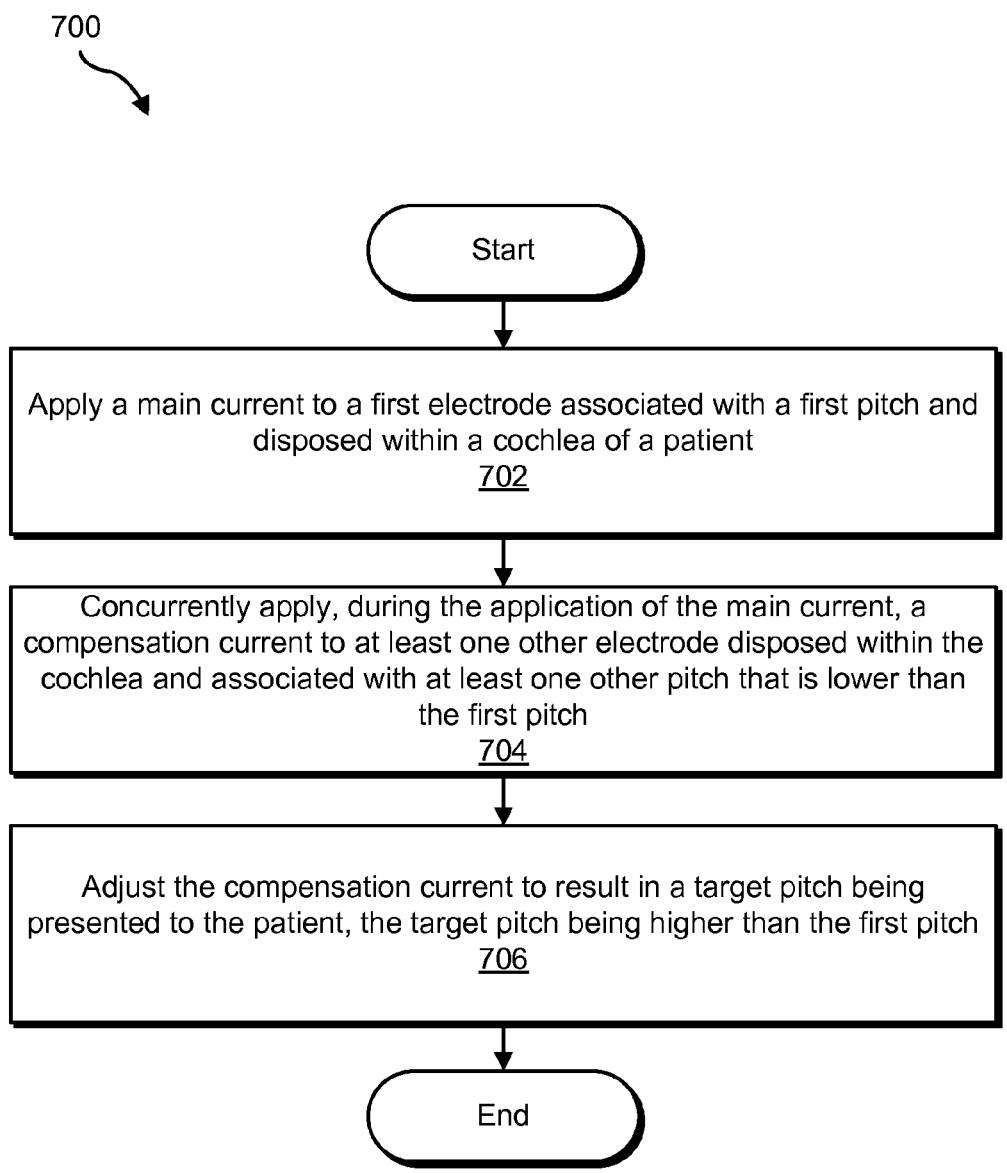
FIG. 7 illustrates an exemplary phantom electrode stimulation method that may be performed by a cochlear implant system according to principles described herein.

For example, FIG. 7 illustrates an exemplary phantom electrode stimulation method 700 that may be performed by cochlear implant system 100 in accordance with a phantom electrode stimulation sound processing program. While FIG. 7 illustrates exemplary steps according to one embodiment, other embodiments may omit, add to, reorder, and/or modify any of the steps shown in FIG. 7. Method 700, as well as other embodiments related to phantom electrode stimulation, is more fully described in co-pending U.S. patent application Ser. No. 12/644,350, entitled "Compensation Current Optimization for Cochlear Implant Systems," filed Dec. 22, 2010, and incorporated herein by reference in its entirety.

In step 702, a main current is applied to a first electrode associated with a first pitch and disposed within a cochlea of a patient. The first electrode may include a most basal electrode included in an array of electrodes disposed in the cochlea or any other electrode included in the electrode array.

In step 704, a compensation current is concurrently applied during the application of the main current to at least one other electrode disposed within the cochlea and associated with at least one other pitch that is lower than the first pitch. The at least one other electrode may include any number of electrodes in the array of electrodes as may serve a particular implementation.

In step 706, the compensation current is adjusted to result in a target pitch being presented to the patient, the target pitch being higher than the first pitch. The compensation current may be adjusted in any of the ways described in the above-referenced co-pending U.S. patent application Ser. No. 12/644,350.

Figure 8:
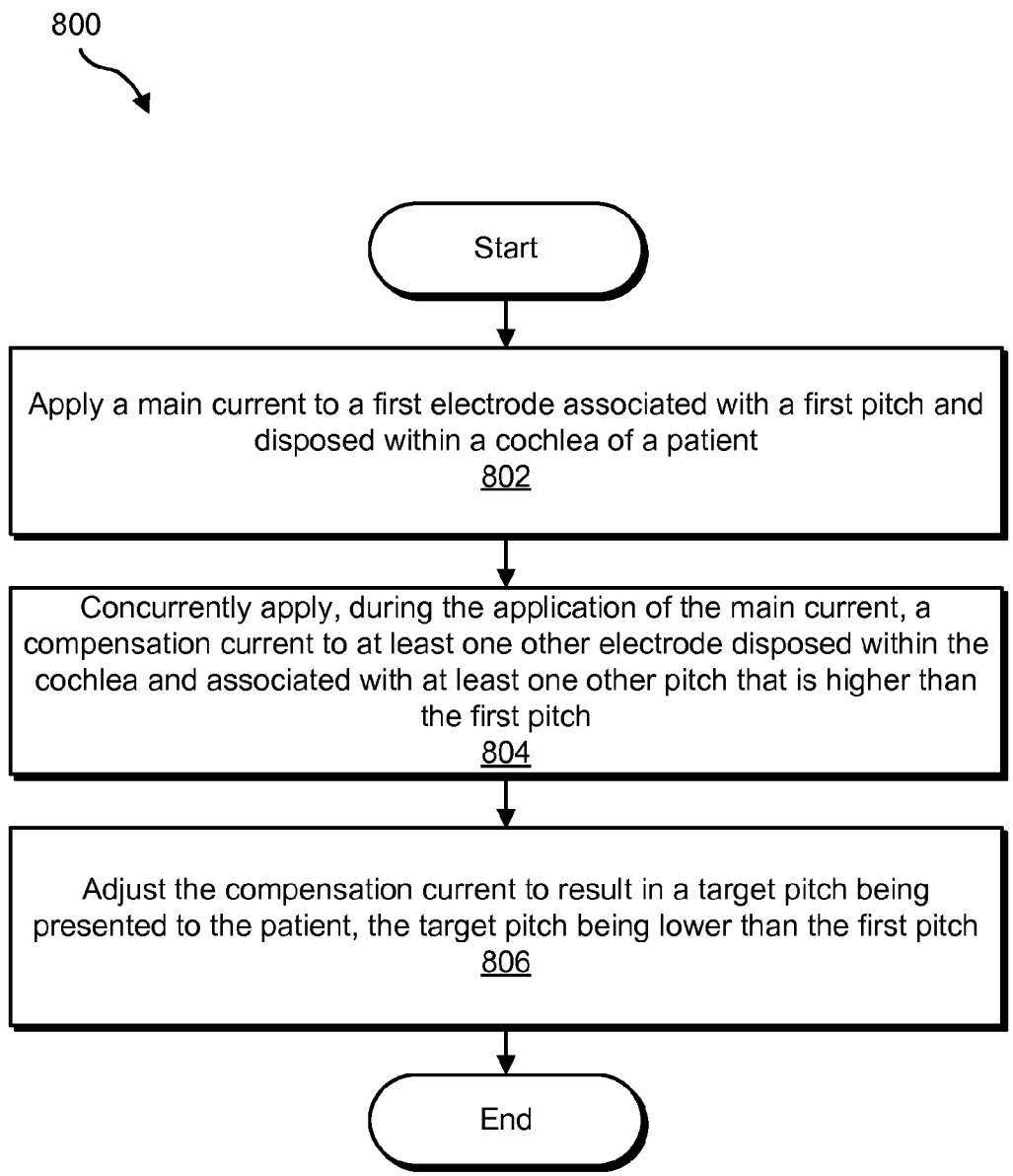
FIG. 8 illustrates another exemplary phantom electrode stimulation method that may be performed by a cochlear implant system according to principles described herein.

FIG. 8 illustrates another phantom electrode stimulation method 800 that may be performed by cochlear implant system 100 in accordance with a phantom electrode stimulation sound processing program. While FIG. 8 illustrates exemplary steps according to one embodiment, other embodiments may omit, add to, reorder, and/or modify any of the steps shown in FIG. 8. Method 800 is more fully described in the above-referenced co-pending U.S. patent application Ser. No. 12/644,350.

In step 802, a main current is applied to a first electrode associated with a first pitch and disposed within a cochlea of a patient. The first electrode may include a most apical electrode included in an array of electrodes disposed in the cochlea or any other electrode included in the electrode array.

In step 804, a compensation current is concurrently applied during the application of the main current to at least one other electrode disposed within the cochlea and associated with at least one other pitch that is higher than the first pitch. The at least one other electrode may include any number of electrodes in the array of electrodes as may serve a particular implementation.

In step 806, the compensation current is adjusted to result in a target pitch being presented to the patient, the target pitch being lower than the first pitch. The compensation current may be adjusted in any of the ways described in the above-referenced co-pending U.S. patent application Ser. No. 12/644,350.

It will be recognized that the exemplary phantom electrode stimulation sound processing programs described in connection with FIGS. 7-8 are merely illustrative of the many different sound processing programs that may be used in conjunction with anode-cathode biphasic stimulation to expand a range of pitches that may be presented to a cochlear implant patient.

Returning to FIG. 3, storage facility 306 may be configured to maintain detection data 308 generated and/or used by detection facility 302 and/or control data 310 generated and/or used by control facility 304. It will be recognized that storage facility 306 may maintain additional or alternative data as may serve a particular implementation.

Figure 9:
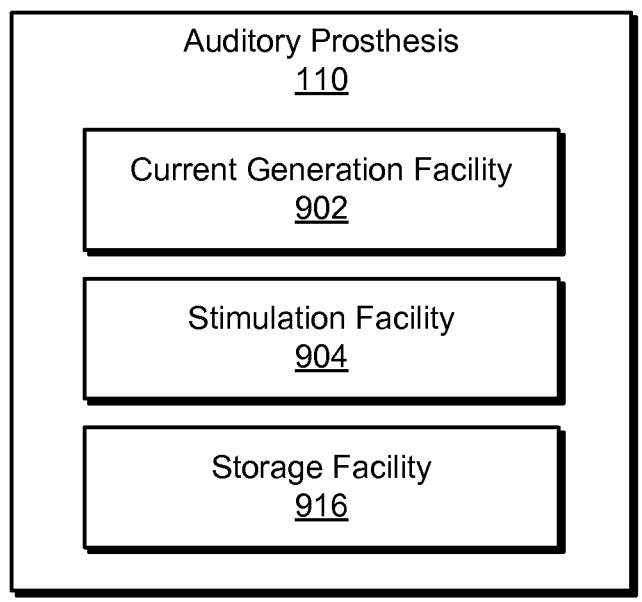
FIG. 9 illustrates exemplary components of a cochlear implant according to principles described herein.

FIG. 9 illustrates exemplary components of cochlear implant 110. As shown in FIG. 9, cochlear implant 110 may include a current generation facility 902, a stimulation facility 904, and a storage facility 906, which may be in communication with one another using any suitable communication technologies.

Current generation facility 902 may be configured to generate stimulation current in accordance with one or more control parameters (received from sound processor 104. To this end, current generation facility 902 may include one or more current generators and/or any other circuitry configured to facilitate generation of stimulation current. For example, current generation facility 902 may include an array of independent current generators each corresponding to a distinct electrode or channel.

Stimulation facility 904 may be configured to facilitate application of the stimulation current generated by current generation facility 902 to one or more stimulation sites within the patient in accordance with one or more stimulation parameters received from sound processor 104. For example, stimulation facility 902 may be configured to apply electrical stimulation pulses to one or more electrodes in accordance with one or more control parameters provided by sound processor 102. To illustrate, stimulation facility 904 may apply one or more anode-cathode biphasic stimulation pulses to the most apical electrode during a stimulation period and one or more cathode-anode biphasic stimulation pulses to one or more other electrodes included in the plurality of electrodes that are disposed within the cochlea during the same stimulation period.

Storage facility 906 may be configured to maintain data generated and/or utilized by cochlear implant 110. For example, storage facility 906 may maintain data representative of one or more control parameters configured to define the stimulation current generated and applied by cochlear implant 110.

Figure 10:
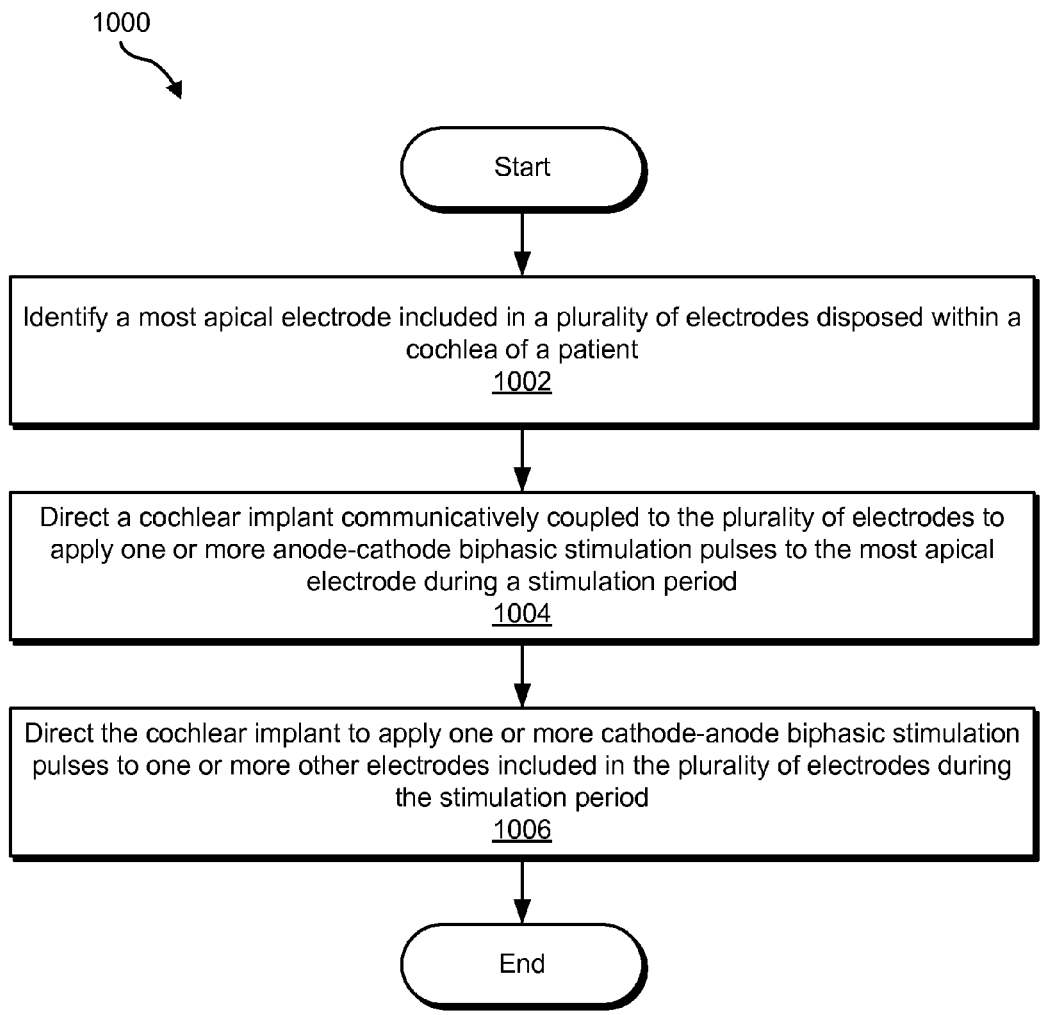
FIG. 10 illustrates an exemplary method of lowering a pitch sensation as perceived by a cochlear implant patient according to principles described herein.

FIG. 10 illustrates an exemplary method 1000 of lowering a pitch sensation as perceived by a cochlear implant patient. While FIG. 10 illustrates exemplary steps according to one embodiment, other embodiments may omit, add to, reorder, and/or modify any of the steps shown in FIG. 10. One or more of the steps shown in FIG. 10 may be performed by sound processor 104 and/or any implementation thereof.

In step 1002, a sound processor identifies a most apical electrode included in a plurality of electrodes disposed within a cochlea of a patient. Step 1002 may be performed in any of the ways described herein.

In step 1004, the sound processor directs a cochlear implant communicatively coupled to the plurality of electrodes to apply one or more anode-cathode biphasic stimulation pulses to the most apical electrode during a stimulation period. Step 1004 may be performed in any of the ways described herein.

In step 1006, the sound processor directs the cochlear implant to apply one or more cathode-anode biphasic stimulation pulses to one or more other electrodes included in the plurality of electrodes during the stimulation period. Step 1006 may be performed in any of the ways described herein.

Figure 11:
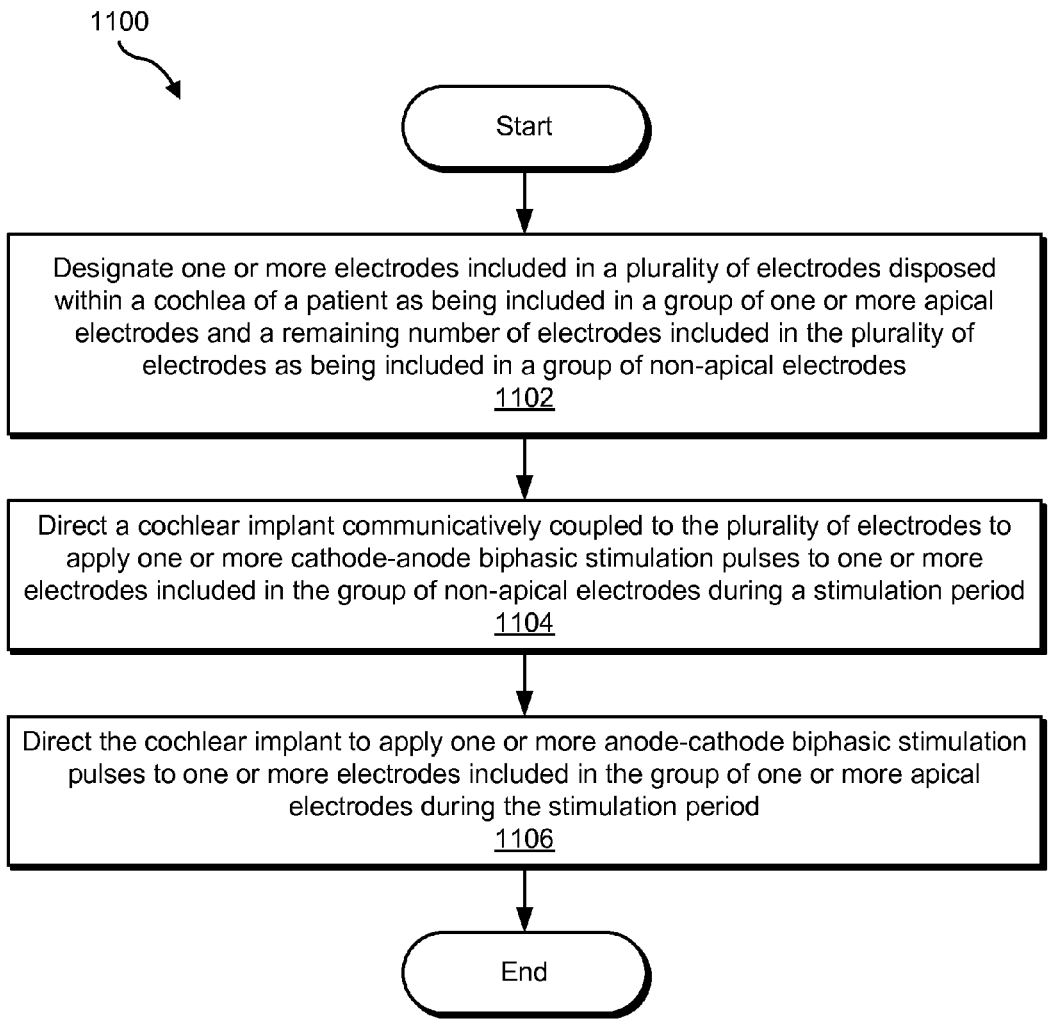
FIG. 11 illustrates another exemplary method of lowering a pitch sensation as perceived by a cochlear implant patient according to principles described herein.

As mentioned, anode-cathode biphasic stimulation pulses may additionally be applied to one or more other electrodes (e.g., one or more electrodes disposed in an apical region of the cochlea). For example, FIG. 11 illustrates another exemplary method 1100 of lowering a pitch sensation as perceived by a cochlear implant patient. While FIG. 11 illustrates exemplary steps according to one embodiment, other embodiments may omit, add to, reorder, and/or modify any of the steps shown in FIG. 11. One or more of the steps shown in FIG. 11 may be performed by sound processor 104 and/or any implementation thereof.

In step 1102, a sound processor designates one or more electrodes included in a plurality of electrodes disposed within a cochlea of a patient as being included in a group of one or more apical electrodes and a remaining number of electrodes included in the plurality of electrodes as being included in a group of non-apical electrodes. Step 1102 may be performed in any of the ways described herein.

In step 1104, the sound processor directs a cochlear implant communicatively coupled to the plurality of electrodes to apply one or more cathode-anode biphasic stimulation pulses to one or more electrodes included in the group of non-apical electrodes during a stimulation period. Step 1104 may be performed in any of the ways described herein.

In step 1106, the sound processor directs the cochlear implant to apply one or more anode-cathode biphasic stimulation pulses to one or more electrodes included in the group of one or more apical electrodes during the stimulation period. Step 1106 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
   identifying, by a sound processor, a most apical electrode included in a plurality of electrodes disposed within a cochlea of a patient;
   directing, by the sound processor, a cochlear implant communicatively coupled to the plurality of electrodes to apply one or more anode-cathode biphasic stimulation pulses to the most apical electrode during a stimulation period, wherein the one or more anode-cathode biphasic stimulation pulses each comprise a positive first phase followed by a negative second phase; and
   directing, by the sound processor, the cochlear implant to apply one or more cathode-anode biphasic stimulation pulses to a plurality of other electrodes included in the plurality of electrodes during the stimulation period, wherein the one or more cathode-anode biphasic stimulation pulses each comprise a negative first phase followed by a positive second phase;

wherein the one or more anode-cathode biphasic stimulation pulses and the one or more cathode-anode biphasic stimulation pulses are equivalent in pulse width.

2. The method of claim 1, wherein the most apical electrode is associated with a pitch, and wherein the directing of the cochlear implant to apply one or more anode-cathode biphasic stimulation pulses to the most apical electrode is configured to result in a pitch being presented to the patient that is lower than the pitch associated with the most apical electrode.

3. The method of claim 1, further comprising:
detecting, by the sound processor, an auditory scene associated with the patient;
wherein the directing of the cochlear implant to apply one or more anode-cathode biphasic stimulation pulses to the most apical electrode is performed in response to the detecting of the auditory scene.

4. The method of claim 3, wherein the auditory scene comprises an auditory scene in which the patient is listening primarily to music.

5. The method of claim 1, further comprising:
detecting, by the sound processor subsequent to the directing of the cochlear implant to apply one or more anode-cathode biphasic stimulation pulses to the most apical electrode, a change in an auditory scene associated with the patient; and
directing, by the sound processor, the cochlear implant to switch to applying one or more cathode-anode biphasic stimulation pulses to the most apical electrode in response to the detecting of the change in the auditory scene.

6. The method of claim 5, wherein the change in the auditory scene comprises a change to an auditory scene in which the patient is listening primarily to speech.

7. The method of claim 1, further comprising:
identifying, by the sound processor, a group of one or more additional electrodes included in the plurality of electrodes that is adjacent to the most apical electrode; and
directing, by the sound processor, the cochlear implant to apply one or more anode-cathode biphasic stimulation pulses to the group of one or more additional electrodes during the stimulation period.

8. The method of claim 1, wherein the plurality of other electrodes included in the plurality of electrodes comprise all of the electrodes included in the plurality of electrodes other than the most apical electrode.

9. The method of claim 1, wherein a duration of the negative second phase is longer than a duration of the positive first phase.

10. The method of claim 9, wherein the duration of the negative second phase is at least twice as long as the duration of the positive first phase.

11. The method of claim 1, further comprising performing the directing of the cochlear implant to apply one or more anode-cathode biphasic stimulation pulses to the most apical electrode in conjunction with a phantom electrode stimulation sound processing program.

12. A method comprising:
designating, by a sound processor, one or more electrodes included in a plurality of electrodes disposed within a cochlea of a patient as being included in a group of one or more apical electrodes and a remaining number of electrodes included in the plurality of electrodes as being included in a group of non-apical electrodes;
directing, by the sound processor, a cochlear implant communicatively coupled to the plurality of electrodes to apply one or more cathode-anode biphasic stimulation pulses to a plurality of electrodes included in the group of non-apical electrodes during a stimulation period, wherein the one or more cathode-anode biphasic stimulation pulses each comprise a negative first phase followed by a positive second phase; and
directing, by the sound processor, the cochlear implant to apply one or more anode-cathode biphasic stimulation pulses to one or more electrodes included in the group of one or more apical electrodes during the stimulation period, wherein the one or more anode-cathode biphasic stimulation pulses each comprise a positive first phase followed by a negative second phase;
wherein the one or more anode-cathode biphasic stimulation pulses and the one or more cathode-anode biphasic stimulation pulses are equivalent in pulse width.

13. The method of claim 12, wherein the group of one or more apical electrodes comprises a most apical electrode included in the plurality of electrodes.

14. The method of claim 12, further comprising:
detecting, by the sound processor, an auditory scene associated with the patient;
wherein the directing of the cochlear implant to apply one or more anode-cathode biphasic stimulation pulses to one or more electrodes included in the group of one or more apical electrodes is performed in response to the detecting of the auditory scene.

15. The method of claim 14, wherein the auditory scene comprises an auditory scene in which the patient is listening to music.

16. The method of claim 12, further comprising:
detecting, by the sound processor subsequent to the directing of the cochlear implant to apply the one or more anode-cathode biphasic stimulation pulses to one or more electrodes included in the group of one or more apical electrodes, a change in an auditory scene associated with the patient; and
directing, by the sound processor in response to the change in the auditory scene, the cochlear implant to switch to applying one or more cathode-anode biphasic stimulation pulses to the one or more electrodes included in the group of one or more apical electrodes.

17. The method of claim 16, wherein the change in the auditory scene comprises a change to an auditory scene in which the patient is listening to speech.

18. The method of claim 12, wherein a duration of the negative second phase is longer than a duration of the positive first phase.

19. A system comprising:
a detection facility configured to identify a most apical electrode included in a plurality of electrodes disposed within a cochlea of a patient; and
a control facility communicatively coupled to the detection facility and configured to
direct a cochlear implant communicatively coupled to the plurality of electrodes to apply one or more anode-cathode biphasic stimulation pulses to the most apical electrode during a stimulation period, wherein the one or more anode-cathode biphasic stimulation pulses each comprise a positive first phase followed by a negative second phase; and
direct the cochlear implant to apply one or more cathode-anode biphasic stimulation pulses to a plurality of other electrodes included in the plurality of electrodes during the stimulation period, wherein the one or more cathode-anode biphasic stimulation pulses each comprise a negative first phase followed by a positive second phase;

wherein the one or more anode-cathode biphasic stimulation pulses and the one or more cathode-anode biphasic stimulation pulses are equivalent in pulse width.

20. The system of claim 19, wherein:

the detection facility is further configured to detect an auditory scene associated with the patient; and the control facility is configured to perform the directing of the cochlear implant to apply one or more anode-cathode biphasic stimulation pulses to the most apical electrode in response to the detection of the auditory scene.

* * * * *